(12) United States Patent
Choi et al.

(10) Patent No.: US 8,362,238 B2
(45) Date of Patent: Jan. 29, 2013

(54) METHOD FOR REFINING OF HIGH PURITY OF TACROLIMUS

(75) Inventors: Byoung-Taek Choi, Suwon-si (KR); Yun-Beom Ham, Shi-heung-si (KR); Seong-Seon Yu, Suwon-si (KR); Kyung-Il Jeong, Gwangmyeong-si (KR); Byung-Sik Kim, Ansan-si (KR)

(73) Assignee: Chongkundang Bio Corporation, Seoul (KR)

( * ) Notice: Subject to any disclaimer, the term of this patent is extended or adjusted under 35 U.S.C. 154(b) by 113 days.

(21) Appl. No.: 12/921,820

(22) PCT Filed: Feb. 25, 2009

(86) PCT No.: PCT/KR2009/000905
§ 371 (c)(1),
(2), (4) Date: Nov. 23, 2010

(87) PCT Pub. No.: WO2009/116729
PCT Pub. Date: Sep. 24, 2009

(65) Prior Publication Data
US 2012/0065393 A1   Mar. 15, 2012

(30) Foreign Application Priority Data
Mar. 17, 2008   (KR) ........................ 10-2008-0024207

(51) Int. Cl.
*C07D 413/00*   (2006.01)
(52) U.S. Cl. ....................................... 540/456
(58) Field of Classification Search .................... 540/456
See application file for complete search history.

(56) References Cited

U.S. PATENT DOCUMENTS

| | | | |
|---|---|---|---|
| 4,916,138 A | 4/1990 | Ueda et al. | |
| 4,929,611 A | 5/1990 | Okuhara et al. | |
| 4,956,352 A | 9/1990 | Okuhara et al. | |
| 5,116,756 A | 5/1992 | Dumont et al. | |
| 5,254,562 A | 10/1993 | Okuhara et al. | |
| 5,496,727 A | 3/1996 | Okuhara et al. | |
| 5,624,842 A | 4/1997 | Okuhara et al. | |
| 5,830,717 A | 11/1998 | Okuhara et al. | |
| 6,492,513 B1 | 12/2002 | Nishihara et al. | |
| 2006/0142565 A1 | 6/2006 | Keri et al. | |
| 2006/0169199 A1 | 8/2006 | Keri et al. | |
| 2007/0142424 A1 | 6/2007 | Vaid | |

FOREIGN PATENT DOCUMENTS

| EP | 0240773 A1 | 10/1987 |
|---|---|---|
| WO | 2006/031664 | 3/2006 |

OTHER PUBLICATIONS

International Search Report mailed in PCT/KR2009/000905 filed Feb. 25, 2009.
Written Opinion of the International Searching Authority mailed Oct. 7, 2009 in PCT/KR2009/000905 filed Feb. 25, 2009.

*Primary Examiner* — Bruck Kifle
(74) *Attorney, Agent, or Firm* — Drinker Biddle & Reath LLP

(57) ABSTRACT

The present invention relates to a process of preparing a highly pure tacrolimus, which comprising a pre-purification process carried out by means of crystallization, and particularly to a process of preparing a highly pure tacrolimus, which comprises a pre-purification process comprising the steps of (a) extracting mycelia cake collected by filtering a tacrolimus-containing oily compound with an organic solvent, (b) concentrating the extract under reduced pressure and (c) crystallizing the concentrate. In addition, a highly pure tacrolimus can be obtained by dissolving the pre-purified crystals in an organic solvent, passing through the solution in an adsorption resin and concentrating the eluate under reduced pressure, followed by crystallization. According to a process of the present invention, Tacrolimus as pure as appropriate for a pharmaceutical purpose can be prepared by a simple process and at a relatively low cost.

14 Claims, 2 Drawing Sheets

|   | Name | Height | Area | %Area |
|---|------|--------|------|-------|
| 1 | Compound A | 15223 | 253553 | 1.08 |
| 2 | Unknown comppund | 5291 | 112247 | 0.48 |
| 3 | Tacrcolimus | 48178 | 877268 | 3.75 |
| 4 | Tautomer II | 1000221 | 22019280 | 94.15 |
| 5 | Compound A | 1467 | 126159 | 0.54 |

METHOD FOR REFINING OF HIGH PURITY OF TACROLIMUS

CROSS REFERENCE TO RELATED APPLICATIONS

This application is the National Stage of International Application No. PCT/KR2009/000905, filed Feb. 25, 2009, and claims benefit of Korean Application No. 10-2008-0024207, filed Mar. 17, 2008, both of which are herein incorporated by reference in their entirety.

TECHNICAL FIELD

The present invention relates to a process of purifying tacrolimus, and particularly to a process which comprises a process of pre-purifying tacrolimus by removing coloring matters or lipids in an extract of a tacrolimus-containing fermentation, followed by crystallization. A highly pure tacrolimus can be prepared by adsorbing the pre-crystallized crude product on a hydrophobic resin and conducting crystallization.

BACKGROUND ART

Tacrolimus is an immunosuppressant and a macrolide antibiotic, 100 times more potent than cyclosporine, which selectively inhibits T-lymphocyte activation. It is widely used for the treatment or prevention of rejection in tissue transplantation, autoimmune disorder and infectious diseases caused by pathogenic microorganism. It has an empirical formula of $C_{44}H_{69}NO_{12}H_2O$ and the following structure.

[Formula I]

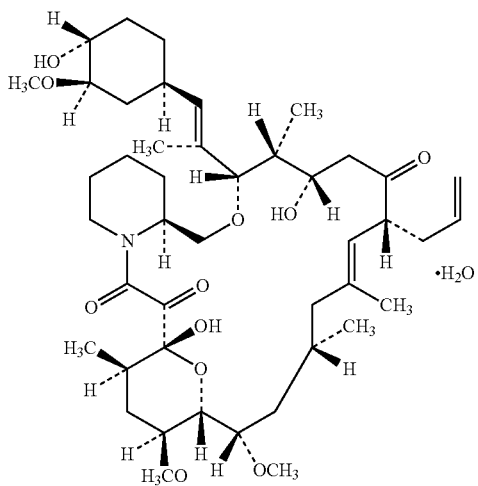

Tacrolimus is prepared by the fermentation of *Streptomyces tsukubaensis* 9993, i.e. monotypic species of *Streptomyces*, as disclosed in U.S. Pat. Nos. 5,496,727, 5,624,842 and 5,830,717. The fermentation of *Streptomyces* sp. produces tacrolimus and also provides 17-ethyl derivative (II) known as ascomycin (FK520) and 17-propyl derivative (III) 17-propyl-1,14-dihydroxy-12-[2-(4-hydroxy-3-methoxycyclohexyl)-1-methylvinyl]-23,25-dimethoxy-13,19,21,27-tetramethyl-11,28-dioxy-4-azatricyclo-[22.3.1.04.9]octacos-18-ene-2,3,10,16-tetraone). Therefore, there have been various methods reported for separating tacrolimus from a cultured broth.

In U.S. Pat. Nos. 4,929,611 and 5,254,562, a cultured broth filtrate and a mycelia cake extract are combined and eluted on a synthetic adsorption resin (Diaion HP-20), followed by a column chromatography, there providing a highly pure tacrolimus (yield 14%). In more detail, an adsorbed material is washed with distilled water and an organic solvent and elution is carried out. An active fraction is concentrated under reduced pressure and extracted with an organic solvent. The extract is concentrated and column-chromatographied with a normal-phase silica gel (70-230 mesh) by using a mixture of ethylacetate and n-hexane mixture (1:9 v/v, 1:4 v/v, 1:1 v/v and 2:1 v/v) and ethylacetate as mobile phase. Active fractions are collected and concentrated, followed by a column chromatography with a normal-phase silica gel (230-400 mesh) by using a mixture of ethylacetate and n-hexane mixture (1:1 v/v and 2:1 v/v) and ethylacetate as mobile phase. The collected active fraction is subjected to a high-pressure liquid chromatography of a crude product by using the same silica gel (70-230 mesh) and solvent. Elution is conducted by using a column (8?×500 mm) equipped with Lichrosory S160 (Merck Co., Ltd.) as a carrier, and such steps are repeated to provide a highly pure tacrolimus.

In U.S. Pat. Nos. 4,916,138, 4,956,352 and 5,830,717 and European patent publication No. 0,240,773 A1, active fractions concentrated as described in U.S. Pat. No. 4,929,611 are dissolved in acetonitrile, and crystallized at 5° C. to provide a highly pure tacrolimus.

However, this purification process requires the repetition of a high-priced HPLC purification or crystallization after complicated steps using a synthetic adsorbent and a normal-phase resin, while showing a relatively low yield (15%) of tacrolimus.

Although tacrolimus is prepared by using an adsorption and reversed phase resin in U.S. Pat. No. 5,116,756, this method is merely for the identification of a target compound, and cannot be applied for an industry-scaled manufacture.

In the meantime, U.S. Pat. No. 6,492,513 discloses a purification method by using a cation-type ion-exchange resin pretreated with silver salt. According to this purification method, a filtrate of oily compound and a mycelia cake extract were combined and adsorbed onto a synthetic adsorption resin (Diaion HP-20), followed by a column chromatography to provide a crude product. Elution was conducted by developing the crude product with acetone on a synthetic adsorption resin pretreated with silver ion (Capcell Pak SCX UG80™, Shiseido Ltd., Japan). This purification is based on a principle that a cation exchange resin adsorbs tacrolimus more strongly than other impurities due to the formation of silver complex. However, although ascomycin (II) and 17-propyl derivative (III) can be separated, other impurities cannot be separated from tacrolimus by using this process. Therefore, tacrolimus product thus prepared is not suitable for a pharmaceutical purpose due to a low purity.

The information disclosed in the above Background section is only for the enhancement of understanding of the background of the invention and therefore it may contain information that does not form the prior art that is already known in this country to a person of ordinary skill in the art.

All publications, patents and patent applications cited herein, whether supra or infra, are hereby incorporated by reference in their entirety to the same extent as if each individual publication, patent or patent application is specifically and individually indicated to be incorporated by reference.

DISCLOSURE OF INVENTION

Technical Problem

To overcome the aforementioned problems, the present inventors have exerted extensive researches, and have ascertained that tacrolimus can be prepared in a high purity and yield by pre-purifying tacrolimus-containing solution through crystallization to give a crude product, passing a solution containing the crude product through a hydrophobic adsorption resin and conducting crystallization. As a result, they have finally completed the present invention, which overcomes the conventional problems such as a complicated process and an economical burden.

The present invention aims to overcome the problems of the conventional processes of purifying tacrolimus such as a complicated process, a relatively high cost and a low yield, and also aims to provide a process of preparing a highly pure tacrolimus that is appropriate for a pharmaceutical purpose.

Technical Solution

The present invention discloses a process of preparing a highly pure tacrolimus, which comprises a pre-purification process carried by extracting a tacrolimus-containing oily compound, removing coloring matters or lipids, conducting a crystallization, concentrating the obtained material and conducting a crystallization.

Advantageous Effects

Through a crystallization step during a pre-purification, tacrolimus can be prepared in a high yield (more than 30%) and a high purity by a simple process where a column chromatography is carried out only once without conducting a high-priced HPLC step as disclosed herein. Therefore, tacrolimus prepared by a purification process of the present invention is suitable for the purpose of drugs.

DESCRIPTION OF DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
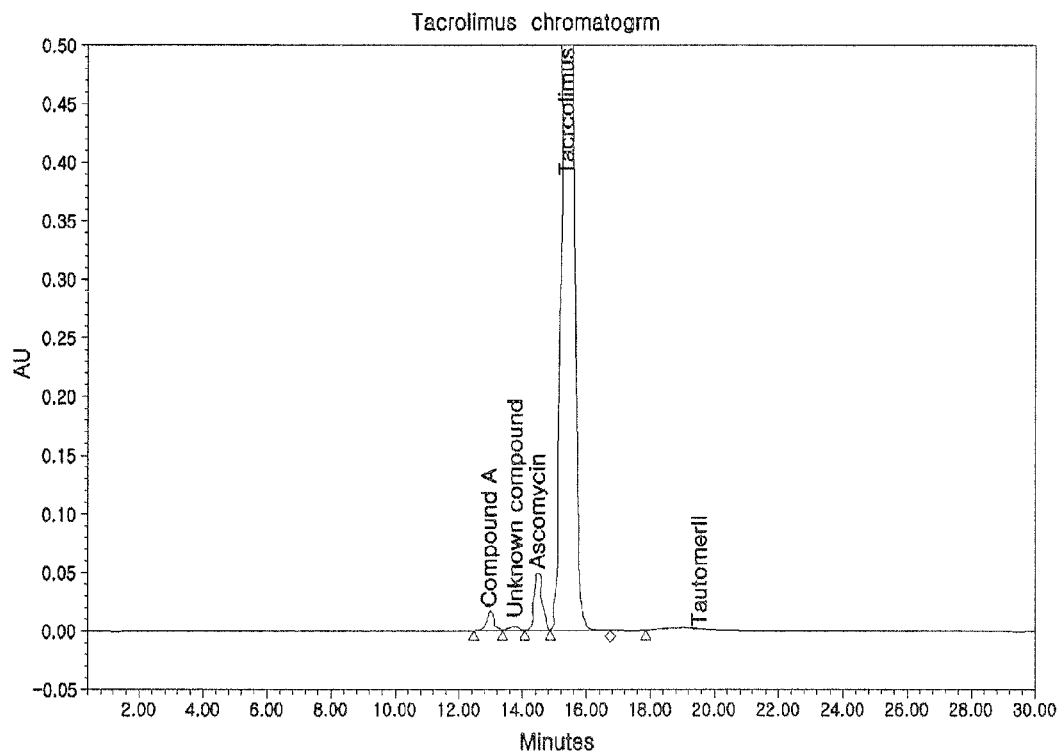
FIG. 1 shows the results of the analysis of tacrolimus crude product after pre-crystallization.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

MODE FOR THE INVENTION

Reference will now be made in detail to the preferred embodiments of the present invention, examples of which are illustrated in the drawings attached hereinafter, wherein like reference numerals refer to like elements throughout. The embodiments are described below so as to explain the present invention by referring to the figures.

The present invention discloses a process of purifying tacrolimus, which comprises a pre-purification process comprising extracting a tacrolimus-containing oily compound, removing coloring matters or lipids, concentrating the extract and conducting crystallization.

Hereunder is provided a detailed description of the present invention.

The present invention relates to a process of preparing a highly pure tacrolimus, which comprises a crystallization-based pre-purification process, and in particular the pre-purification is conducted by extracting mycelia cake collected by conducting a diatomite coating filtration of a tacrolimus-containing oily compound with an organic solvent, concentrating the extract under reduced pressure and crystallizing the concentrate. In addition, a highly pure tacrolimus can be obtained by dissolving the pre-purified crystals in an organic solvent, eluting the solution on an adsorption resin, concentrating the eluate under reduced pressure and conducting crystallization.

As used herein, the terms of 'filtration', 'extraction', 'concentration' and 'crystallization' include techniques known to those skilled in the art.

A tacrolimus-containing oily compound may be prepared by the fermentation of *Streptomyces tsukubaensis* 9993, i.e. monotypic species of *Streptomyces*, as disclosed in U.S. Pat. Nos. 5,496,727, 5,624,842 and 5,830,717. The fermentation of *Streptomyces* sp. produces ascomycin (FK520) and 17-propyl derivative (III) as well as tacrolimus, and impurities such as lipids and coloring matters are also contained in the product.

A purification process of the present invention comprises a pre-purification process carried by extracting a tacrolimus-containing cultured broth, removing coloring matters or lipids, concentrating the obtained solution and conducting crystallization, thus providing a crude product.

In an embodiment, the pre-purification comprises the steps of:

(a) collecting mycelia cake by conducting diatomite coating filtration of a tacrolimus-containing oily compound;

(b) extracting the collected mycelia cake with an organic solvent and concentrating the extract under reduced pressure;

(c) diluting the concentrate in an organic solvent removing coloring matters or lipids; and (d) conducting a concentration under reduced pressure and a crystallization.

In the step (a), the filtration is conducted by controlling the pH of the tacrolimus-containing fermentation to 2-6, preferably 3-4, more preferably 3.5. A diatomite coating filtration was used in Examples herein.

In the step (b), examples of an organic solvent used for the extraction include without limitation methanol, ethanol, n-propanol, iso-propanol, n-butanol, iso-butanol, tert-butanol, 2-butanol, acetone, acetonitrile, tetrahydrofuran, isobutyl acetate, n-butyl acetate, ethylformate, n-propyl acetate, iso-propyl acetate, methyl-ethyl ketone and a mixture thereof. Among them, methyl alcohol is preferred.

The extraction is carried out by conducting filtration, concentration and re-extraction with an organic solvent. Examples of an organic solvent used for the re-extraction include without limitation chloroform, tetrachloromethane, dichloromethane and methylene chloride, and methylene chloride is preferred.

As used herein, the term of reduced pressure refers to a pressure of lower than about 760 mmHg.

In the step (c), the concentrate is diluted with an extraction solvent, and the diluted solution is passed through an active aluminum oxide (Aluminum Oxide Activated) or silica gel column to remove coloring matters or lipids. Although an active aluminum oxide (75 μm, 200 mesh, WAKO) and a normal-phase silica gel column (70-230 mesh, 10 L) are preferred, another active aluminum oxide or silica gel column may be used without limitation in the present invention only if it can sufficiently remove coloring matters or lipids.

In the step (d), the eluate is concentrated under reduced pressure into 20 vol %, preferably 5-10 vol % of the initial volume of the eluate. In a preferred embodiment, the concentrate is stirred at room temperature for an hour, added with water in an amount of 1% of the volume of the concentrate and stirred at 5° C. for 6 hours. Bright yellow crystalline powder thus prepared is filtered washed with an organic solvent to remove remaining coloring matters and oily substances, thereby providing pre-purified tacrolimus (FIG. 1). Examples of an organic solvent used for washing include without limitation cyclohexane, pentane, n-hexane, heptane, n-octane, iso-octane and methylcyclohexane.

As used herein, the term of 'room temperature' refers to a temperature of about 10-35° C.

Crude product of tacrolimus pre-purified through crystallization has a purity of 92-95%.

In addition, a purification process of the present invention can further comprise dissolving a tacrolimus crude product prepared by conducting the aforementioned crystallization-based pre-purification process in an organic solvent, eluting the solution on an adsorption resin and conducting a crystallization.

In an embodiment, the crystallization of fractions eluted after the adsorption on an adsorption resin comprises the steps of:

(a') dissolving a tacrolimus crude product produced in a pre-crystallization in an organic solvent;

(b') conducting an elution by adsorbing the solution of a crude product on an adsorption resin and conducting a column chromatography;

(c') adding an organic solvent to an elution fraction for a phase transfer and conducting an extraction; and (d') concentrating the extract under reduced pressure and conducting a crystallization.

In the step (a'), examples of an organic solvent include without limitation ethyl acetate, methanol, ethanol, n-propanol, iso-propanol, n-butanol, iso-butanol, tert-butanol, 2-butanol, acetone, acetonitrile, tetrahydrofuran, isobutyl acetate, n-butyl acetate, ethylformate, n-propyl acetate, iso-propyl acetate, methyl-ethyl ketone and a mixture thereof, and acetonitrile is preferred.

In the step (b'), a tacrolimus crude product dissolved in an organic solvent is adsorbed a column filled with an adsorption resin and eluted according to a column chromatography by using acetonitrile and water as a mobile phase. Any known column chromatography can be adopted and the use of HPLC is not required in the present invention.

Although a preferable ratio of between acetonitrile and water is 4:6 v/v, 5:5 v/v or 6:4 v/v at pH 3.0, any ratio that can facilitate the elution can be adopted in the present invention.

In an embodiment, it is preferred that an adsorption resin has the following characteristics. Preferably, an adsorption resin is hydrophobic and has a pore size of 100-150 Å and a surface area of 700-1,200 m$^2$/g. More preferably, an adsorption resin is a polystyrene-based or divinylbenzene-based hydrophobic adsorption resin for a low-pressure chromatography, which is resistant to a solvent, acidity and alkalinity and has a particle diameter of 35-150 μm, preferably of 75 μm.

Examples of an adsorption resin include without limitation a resin with combining carbon on silica gel substrate such as Daisogel IR-60-63/210-ODS-A (DAISO CO., LTD), Daisogel IR-120-40/60-ODS-A (DAISO CO., LTD) and DMS DM 1020 (Shiseido co.), which have a particle diameter of 50-150 μm, 30-70 μm and 50-150 μM, respectively. In an embodiment, a hydrophobic adsorption resin (Amberchrom CG161M, Rohm and Haas company) having a particle diameter of 75 μm is most preferred without limiting the scope of the present invention.

In the step (c'), examples of an organic solvent include without limitation chloroform, tetrachloromethane, dichloromethane and methylene chloride, and methylene chloride is preferred.

In the step (d'), an extract is concentrated under reduced pressure into 20 vol %, preferably 5-10 vol % of the initial volume of an extract. Examples of an organic solvent for the concentration include without limitation ethyl acetate, methanol, ethanol, n-propanol, iso-propanol, n-butanol, iso-butanol, tert-butanol, 2-butanol, acetone, acetonitrile, tetrahydrofuran, isobutyl acetate, n-butyl acetate, ethylformate, n-propyl acetate, iso-propyl acetate, methyl-ethyl ketone and a mixture thereof, and acetonitrile is preferred. Concentrate is dissolved in an organic solvent and filtered, followed by a crystallization at a low temperature. Crystallization here can be conducted as described in the pre-purification process.

Figure 2:
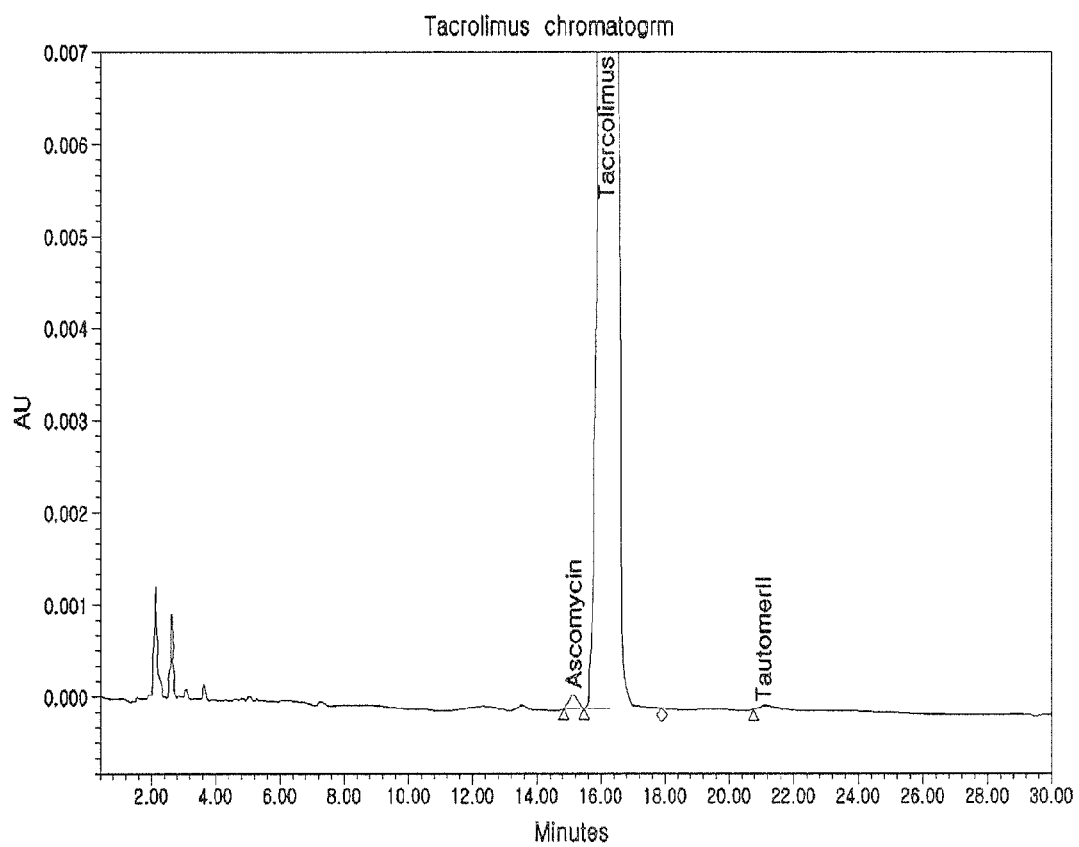
FIG. 2 shows the results of the analysis of tacrolimus product prepared by eluting the pre-crystallite solution on a hydrophobic resin and conducting crystallization.

A crystallized product is filtered to recover powders, and the filtrate is recrystallized to provide a white powder. The obtained powder is vacuum-dried at 45-50° C., thereby finally providing a purified tacrolimus (FIG. 2). Thus obtained tacrolimus is stored at a relatively low temperature.

As used herein, the term of 'a low temperature' refers to a temperature of lower than 25° C., preferably from −5° C. to 5° C.

Tacrolimus is finally obtained by the crystallization in a yield of 30-35%, and the purity of thus obtained tacrolimus is 98.5-99.9%, preferably 99% or higher.

The present invention also aims to provide a pharmaceutical composition comprising tacrolimus prepared by the purification process of the present invention. Tacrolimus of the present invention can be administered in the form of a pharmaceutically acceptable salt thereof, and used alone or in combination with other pharmaceutically active compounds.

A pharmaceutical composition comprising tacrolimus prepared according to the present invention can be formulated by a conventional process into a dosage form for oral, topical or suppository administration or into a sterile injection solution. Examples of such dosage forms include without limitation powders, granules, tablets, capsules, suspension, emulsion, syrup and aerosol.

A pharmaceutical composition of the present invention may comprise at least one pharmaceutically acceptable additive such as an excipient, a carrier and a diluent. Examples of such a additive include without limitation lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrysalline cellulose, polyvinylpyrrolidone, water, methyl hydroxybenzoate, propyl hydroxybenzoate, talc, magnesium stearate and mineral oil. Conventional diluents or excipients such as a filler, a bulking agent, a binder, a wetting agent, a disintegrant and a surfactant can be used for the formulation. Examples of a solid form for oral administration include without limitation tablets, pills, powders, granules and capsules. Such a solid form is prepared by mixing an active compound with at least excipient such as starch, calcium carbonate, sucrose, lactose and gelatin. Diluents such as magnesium stearate and talc can also be used. Examples of a liquid form for oral administration include without limitation a suspension, an oral solution, an emulsion and a syrup. Such a liquid form can comprises various excipients (e.g., a wetting agent, a sweetener, a flavoring agent and a preservative) as well as common diluents (e.g., water and liquid paraffin).

EXAMPLES

The following examples illustrate the invention and are not intended to limit the same.

Example 1

The pH of a tacrolimus-containing oily compound 6 L (containing 3.0 g of tacrolimus) was adjusted to 3.5. The mycelia cake was collected by conducting a diatomite coating filtration of the oily compound. After the collected mycelia cake was extracted with methyl alcohol (3 L), methylene chloride 3 L was added to the filtrate, thus conducting extraction and purification. The extract was concentrated under reduced pressure. The concentrate 1 L was diluted with methylene chloride (1:1 v/v) and passed through alumina (1,000 mL) to remove coloring matters and oily substances. The eluate (2 L) was concentrated under reduced pressure to remove methylene chloride, and water (3 mL) was added to the concentration, followed by crystallization at 15° C. and filtration through Nutsche filter. The obtained powder (2.1 g) was washed with n-hexane to remove remaining coloring matters and oily substances and dried, thereby providing a pre-purified specimen (purity 94.1%, yield 72%).

The powder was dissolved in acetonitrile (5 mL), adsorbed onto a column (diameter 1.4 cm, length 30 cm) packed with hydrophobic adsorption resin 30 mL (Amberchrom CG161M, Rohm and Haas company), and developed by using various mixtures of acetonitrile and water (4:6 v/v, 5:5 v/v and 6:4 v/v; pH 3.0) as a mobile phase. The active fraction was added with methylene chloride for phase transfer and extracted, followed by the concentration under reduced pressure. The concentrate (1.5 g) was dissolved in acetonitrile, filtrated and crystallized at a temperature of 4° C. or lower. The obtained crystals were filtered through the crystallization and vacuum-dried to provide white powder, tacrolimus 0.98 g (purity 99.6%, yield 32.7%).

Example 2

The pH of a tacrolimus-containing oily compound 60 L (containing 30 g of tacrolimus) was adjusted to 3.5. Mycelia cake was collected by conducting a diatomite coating filtration of the oily compound. After the collected mycelia cake was extracted with methyl alcohol (30 L), methylene chloride 30 L was added to the filtrate, thus conducting extraction and purification. The extract was concentrated under reduced pressure. The concentrate 10 L was diluted with methylene chloride (1:1 v/v) and passed through normal-phase silica gel (70-230 mesh, 10 L) to remove coloring matters and oily substances. The eluate (20 L) was concentrated under reduced pressure to remove methylene chloride, and water (30 mL) was added to the concentration, followed by crystallization at 15° C. and filtration through Nutsche filter. The obtained powder (22 g) was washed with n-hexane to remove remaining coloring matters and oily substances and dried, followed by crystallization, thereby providing a pre-purified specimen (purity 94.2%, yield 73.3%) in a crude powder state.

The powder was dissolved in acetonitrile (20 mL), adsorbed onto a column (diameter 3 cm, length 65 cm) packed with hydrophobic adsorption resin 300 mL (Amberchrom CG161M, Rohm and Haas company), and developed by using various mixtures of acetonitrile and water (4:6 v/v, 5:5 v/v and 6:4 v/v; pH 3.0) as a mobile phase. The active fraction was added with methylene chloride for phase transfer and extracted, followed by the concentration under reduced pressure. The concentrate (15 g) was dissolved in acetonitrile, filtrated and crystallized at a temperature of 4° C. or lower. The obtained crystals were filtered through the crystallization and vacuum-dried to provide white powder, tacrolimus 10.3 g (purity 99.7%, yield 34.3%).

Example 3

The pre-purified tacrolimus specimen (200 g, purity 92.4%) in a crude powder state obtained through the crystallization was dissolved in acetonitrile (200 mL), adsorbed onto the upper part of a column (diameter 5 cm, length 100 cm) packed with hydrophobic adsorption resin 3 L (Amberchrom CG161M, Rohm and Haas company), and developed by using various mixtures of acetonitrile and water (4:6 v/v, 5:5 v/v and 6:4 v/v; pH 3.0) as a mobile phase. The active fraction was added with methylene chloride for phase transfer and extracted, followed by the concentration under reduced pressure. The concentrate (153 g) was dissolved in acetone, filtrated and crystallized preferably at a temperature of 4° C. or lower. The obtained crystals were filtered through the crystallization and vacuum-dried to provide white powder, tacrolimus 102 g (purity 99.5%, yield 34.0%).

Comparative Example

A pre-purified tacrolimus crude product with a purity of 92% or higher was prepared through crystallization according to the purification method disclosed in the present invention as shown in FIGS. 1 and 2. The crude product was passed through an adsorption resin, and crystallized to provide a highly pure tacrolimus with a purity or 99% or higher.

U.S. Pat. No. 6,492,513 discloses a purification method by using a cation-type ion-exchange resin pretreated with silver salt. According to this purification method, a filtrate of oily compound and a mycelia cake extract were combined and adsorbed onto a synthetic adsorption resin (Diaion HP-20), followed by a column chromatography to provide a crude product with a purity of 85.4%. Elution was conducted by developing the crude product with acetone on a synthetic adsorption resin pretreated with silver ion (Capcell Pak SCX UG80™, Shiseido Ltd., Japan), thereby providing tacrolimus with a purity of 92.7%.

TABLE 1

|  |  | Tacrolimus | Ascomycin | Compound A |
|---|---|---|---|---|
| The present invention | Purity of crude product | 94.15% | 3.75% | 1.08% |
|  | Purity of Tacrolimus | 99.75% | 0.11% | ND |
| U.S. Pat. No. 6,492,513 | Purity of crude product | 85.4% | 5.45% | 1.30% |
|  | Purity of tacrolimus | 92.7% | 0.11% | ND |

Compound A: 17-propyl derivative (III)
(17-propyl-1,14-dihydroxy-12-[2-(4-hydroxy-3-methoxycyclohexyl)-1-methylvinyl]-23,25-dimethoxy-13,19,21,27-tetramethyl-11,28-dioxy-4-azatricyclo-[22.3.1.04.9]octacos-18-ene-2,3,10,16-tetraone)
ND: Not detected The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

The invention claimed is:

1. A process of purifying tacrolimus, comprising:
   (a) collecting mycelia cake in conducting diatomite coating filtration of a tacrolimus-containing oily compound;
   (b) extracting the collected mycelia cake with a first organic solvent to obtain a mycelia cake extract,
   (c) concentrating the mycelia cake extract under reduced pressure to obtain a concentrate;
   (d) diluting the concentrate in a second organic solvent to obtain a dilute solution;
   (e) a chromatography step comprising removing at least one of a coloring matter and lipid by passing the dilute solution through an active aluminum oxide column or a silica gel column to obtain an eluate, wherein the dilute solution has not undergone any prior chromatography step;
   (f) concentrating the eluate under reduced pressure to obtain a concentrated eluate;
   (g) crystallizing the concentrated eluate to obtain a crude tacrolimus.

2. The process of claim 1, wherein the crude tacrolimus has a purity of 92-95%.

3. The process of claim 1, wherein the tacrolimus-containing oily compound is prepared by fermentation of *Streptomyces* sp.

4. A process of purifying the crude tacrolimus of claim 1, comprising;
   (a') dissolving the crude tacrolimus in a third organic solvent to obtain a crude tacrolimus solution;
   (b') absorbing the crude tacrolimus solution onto an absorption resin, and conducting column chromatography on the crude tacrolimus solution to obtain at least one elution fraction:
   (c') adding a fourth organic solvent to at least one elution fraction to obtain an organic extract;
   (d') concentrating the organic extract under reduced pressure, and then crystallizing the concentrated extract to obtain recrystallized tacrolimus.

5. The process of claim 1, wherein the first organic solvent selected from the group consisting of:
   ethyl acetate, methanol, ethanol, n-propanol, iso-propanol, n-butanol, iso-butanol, tert-butanol, 2-butanol, acetone, acetonitrile, tetrahydrofuran, isobutyl acetate, n-butyl acetate, ethylformate, n-propyl acetate, iso-propyl acetate, methyl-ethyl ketone, and a mixture thereof.

6. The process of claim 4, wherein the adsorption resin is a hydrophobic polystyrene-based or divinylbenzene-based resin having a pore size of 100-150 Å, a surface area of 700-1,200 $m^2/g$, and a particle diameter of 35-120 μm.

7. The process of claim 1, wherein the mycelia cake extract is re-extracted in a fifth organic solvent selected from the group consisting of: chloroform, tetrachloromethane, and methylene chloride.

8. The process of claim 4, wherein the recrystallized tacrolimus has a purity of 98.5-99.9%.

9. The process of claim 4, wherein the fourth organic solvent is selected from the group consisting of: chloroform, tetrachloromethane, and methylene chloride.

10. The process of claim 1, wherein the crude tacrolimus has a purity of 98,5-99,9%.

11. The process of claim 3, wherein the crude tacrolimus has a purity of 98.5-99.9%.

12. The process of claim 4, wherein the recrystallized tacrolimus has a purity of 98.5-99.9%.

13. The process of claim 5, wherein the recrystallized tacrolimus has a purity of 98.5-99.9%.

14. The process of claim 6, wherein the recrystallized tacrolimus has a purity of 98.5-99.9%.

* * * * *